United States Patent [19]

Pettijohn et al.

[11] Patent Number: 5,233,114
[45] Date of Patent: Aug. 3, 1993

[54] ALKENE ADDITION PROCESS

[75] Inventors: Ted M. Pettijohn; Mark E. Lashier; Henry L. Hsieh, all of Bartlesville, Okla.

[73] Assignee: Phillips Petroleum Company, Bartlesville, Okla.

[21] Appl. No.: 796,167

[22] Filed: Nov. 22, 1991

[51] Int. Cl.⁵ .............................. C07C 2/30
[52] U.S. Cl. .................. 585/511; 585/516; 502/155; 502/157
[58] Field of Search ............ 502/155; 585/511, 516

[56] References Cited

U.S. PATENT DOCUMENTS

| | | | |
|---|---|---|---|
| 3,356,754 | 12/1967 | Wefford | 260/669 |
| 3,451,988 | 6/1969 | Langer | 585/511 X |
| 3,458,586 | 7/1969 | Langer, Jr. | 260/668 |
| 3,632,663 | 1/1972 | Grebbell et al. | 585/511 |
| 3,674,895 | 7/1972 | Gaerir et al. | 502/155 X |
| 3,751,501 | 8/1973 | Kamienski et al. | 260/668 |
| 3,916,019 | 10/1975 | Closson et al. | 585/511 |
| 4,280,927 | 7/1981 | Loar | 502/155 |
| 4,316,820 | 2/1982 | Wieder et al. | 252/431 N |

*Primary Examiner*—Patrick P. Garvin
*Attorney, Agent, or Firm*—Carl D. Corvin

[57] ABSTRACT

A process is provided comprising contacting a hydrocarbyl alkali metal compound with a nitrogen-containing compound in the presence of propylene. Optionally, a catalytic support is used during said contacting. Optionally, at least one other alpha-olefin is present during said contacting.

In another embodiment a process is provided comprising: (a) contacting a hydrocarbyl alkali metal compound with a nitrogen-containing compound in the presence of propylene; and thereafter (b) recovering an allyl/alkali metal/nitrogen complex; and thereafter (c) contacting said allyl/alkali metal/nitrogen complex with at least one alpha-olefin. Optionally, a catalytic support is present during steps a, b, and c.

12 Claims, No Drawings

ALKENE ADDITION PROCESS

BACKGROUND OF THE INVENTION

This invention relates to a process for the addition of an alkene to another compound.

Alkylation, in general, is a process involving the addition of an alkyl group. Specifically, the term is used in the art to apply to various methods, including both thermal and catalytic processes, for bringing about the union of paraffinic hydrocarbons with olefins. Alkylation reactions are important throughout synthetic organic chemistry. For example, the process is especially effective in yielding gasolines of high octane number and low boiling range which are useable as aviation fuels.

Dimerization, in general, is a process involving the addition of an alkene to another alkene which has the same molecular structure. Dimerization processes are important in organic chemistry for a variety of reasons. For example, dimerization reactions are used to form higher alpha-olefins from lower alpha-olefins thereby providing higher molecular weight monomers which can then be polymerized. For example, propylene can be dimerized to form 4-methyl-1-pentene which in turn can be polymerized into poly(4-methyl-1-pentene). Currently, a preferred method in the art to perform dimerization reactions involves using an alkali metal on an alkali metal carbonate. However, these alkali metal/alkali metal carbonate catalyst systems tend to suffer from severe degradation which can lead to reactor plugging and shorter catalyst life. Additionally, it has been theorized that the conversion of the alkali metal to an active species can result in the expansion of the alkali metal in the alkali metal carbonate to the point that the catalytic system starts to break down. Therefore, methods to produce a catalytically active species without the use of an elemental alkali metal would be both scientifically and economically valuable.

SUMMARY OF THE INVENTION

It is an object of this invention to provide an improved alkene addition process.

It is another object of this invention to provide an improved dimerization process.

These and other objects of this invention will become apparent to those skilled in the art from the following detailed description of the invention.

In accordance with this invention, a process is provided comprising contacting a hydrocarbyl alkali metal compound with a nitrogen-containing compound in the presence of propylene. Optionally, a catalytic support is used during said contacting. Optionally, at least one other alpha-olefin is present during said contacting.

In accordance with another embodiment of this invention a process is provided comprising: (a) contacting a hydrocarbyl alkali metal compound with a nitrogen-containing compound in the presence of propylene; and thereafter (b) recovering an allyl/alkali metal/nitrogen complex; and thereafter (c) contacting said allyl/alkali metal/nitrogen complex at least one alpha-olefin. Optionally, a catalytic support is present during steps a, b, and c.

DETAILED DESCRIPTION OF THE INVENTION

Hydrocarbyl Alkali Metal Compound

The hydrocarbyl alkali metal compounds useful in forming the allyl/alkali metal/nitrogen complexes used in this invention can be characterized as follows. The hydrocarbyl group of the hydrocarbyl alkali metal compound can be a linear or branched alkyl or aryl and can contain from 1 to 20 carbon atoms in the molecule. More preferably, the hydrocarbyl group contains from 2 to 16 carbon atoms and most preferably the hydrocarbyl group contains from 3 to 12 carbon atoms in the molecule. However, it is preferred that the hydrocarbyl group be non-reactive in an alkene addition reaction. This means, in general, that the hydrocarbyl group should not contain any oxygen atoms, nor acid groups, which could interfere with the alkene addition reaction. Examples of suitable hydrocarbyl alkali metal compounds useful in this invention, are methyl lithium, ethyl lithium, propyl lithium, butyl lithium, butyl sodium, butyl potassium, butyl rubidium, butyl cesium, benzyl, lithium, and phenyl lithium.

Nitrogen Containing Compound

The nitrogen-containing compounds useful in forming the allyl/alkali metal/nitrogen complexes used in this invention can be characterized by one of the general formulas shown below.

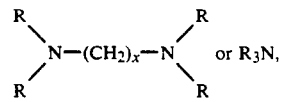

wherein each R group is independently selected from the group consisting of hydrogen and alkyl radicals of 1 to 20 carbon atoms inclusive and X is an integer between 1 and 10 inclusive. However, it is preferred that the alkyl radicals be non-reactive in an alkene addition reaction. This means, in general, that the alkyl radical should not contain any oxygen atoms, nor any acid groups, which could interfere with the alkene addition reaction. Examples of suitable nitrogen-containing compounds, conforming to the general formulas above are N,N,N',N'-tetramethylethylenediamine, N,N,N',N'-tetramethylmethylenediamine, N-methylpyrrolidine, N-methylpiperidine, triethylamine, and trimethylamine. Other examples of compounds useful in this invention which do not conform to the above formula are N,N,N',N'-tetramethyl-1,3-butanediamine, N,N'-dimethyl-1,4-piperazine, triethylenediamine, sparteine, and N,N,N',N', -tetramethyl-1,2-cyclohexanediamine. While these compounds and formulas have been provided as a guide to the types of compounds that will work, the essential feature of these compounds is their ability to form a substantially stable resonance group complex with an alkali metal.

Alpha-Olefin Compounds

The alpha-olefin compounds useful in this invention can be characterized by the following:

(1) the alpha-olefin should have between 3 and 20 carbon atoms inclusive in the molecule;

(2) the alpha-olefin should not contain any oxygen atoms or acid groups, and (3) the alpha-olefin can be linear or branched.

Examples of suitable alpha-olefins useful in this invention include, but are not limited to, propylene, isobutylene, 1-butene, 3-methyl-1-butene, 1-pentene, 3-methyl-1-pentene, 4-methyl-1-pentene, 1-hexene, 3-ethyl-1-hexene, 1-octene, 1-decene, and mixtures thereof.

Procedures to Make the Allyl/Alkali Metal/Nitrogen Complexes

In general, the process of forming an allyl/alkali metal/nitrogen complex is accomplished by contacting a hydrocarbyl alkali metal compound (as disclosed above) with a nitrogen-containing compound (as disclosed above) in the presence of propylene. This reaction yields, in general, a hydrocarbon and an allyl/alkali metal/nitrogen complex. The mole ratio of nitrogen-containing compound to the hydrocarbyl alkali metal should be in the range of about 20:1 to about 1.20. Preferably, the mole ratio is in the range of about 10:1 to about 1:10, most preferably it is in the range of 5:1 to 1:5, and especially preferably it a mole ratio of 3:1 to 0.5:1.

The reaction conditions to form these types of compounds are as follows. The temperature of the reaction should be between about $-50°$ C. to about $350°$ C., preferably between $0°$ C. to $200°$ C., and most preferably between $20°$ C. to $150°$ C. The pressure that the reaction can take place at is from about atmospheric to about 10,000 psig, preferably from atmospheric to about 2,000 psig, and most preferably from atmospheric to 1,000 psig. Additionally, this reaction can take place in a solvent provided the solvent is relatively inert and free of compounds which would tend to interfere with the alkene addition reaction. That is, the solvent should be substantially free of compounds which contain acid groups, water or oxygen.

Reacting the Allyl/Alkali Metal/Nitrogen Complex

After the allyl/alkali metal/nitrogen complex is formed it can be used either in situ or it can be separated and stored for later use. The allyl/alkali metal/nitrogen complex and an alpha-olefin (as disclosed above) can be reacted under the same conditions stated above for forming the allyl/alkali metal/nitrogen complex. An example of an in situ process would be the reacting of n-butyl lithium and tetramethylethylenediamine in an excess of propylene (an excess is a molar ratio of propylene to lithium of greater than 1:1 but less than 100:1). In general, these compounds would react to yield n-butane, an allyl/lithium/tetramethylethylenediamine complex, and 4-methyl-1-pentene which is a dimerization product of propylene. An example of a two-step process would be using the reactants above with only a slight amount of propylene (a slight amount is a molar ratio of propylene to lithium of less than 1:1 but greater than 1:100). An allyl/alkali metal/tetramethylethylenediamine complex would form which could be recovered and stored for later use. This recovered product can be reacted with an alpha-olefin (as described above) to form an alkene addition product. Specifically, if propylene is then added to the allyl/alkali metal/nitrogen complex, 4-methyl-1-pentene would be formed.

Catalytic Support

Regardless of how the above reaction is conducted a catalytic support can be used in the reaction also. The term "catalytic support" is defined as a composition useful in increasing the entire catalytic system's productivity and value, it is not meant to be construed as an inert composition which lends nothing to the catalytic system. A catalytic support would allow the catalyst to precipitate on and/or impregnate the catalytic support. This would provide an improved catalytic system and reaction site. Examples of catalytic supports are alkali metal carbonates; silica; alumina, silica-alumina, and alumina-phosphates. These catalytic supports are broadly known in the art and are disclosed, for example, in U.S. Pat. Nos. 4,544,790; 4,609,637; 4,656,154; 4,982,043; 4,988,658; 5,001,204; 5,021,379; and 5,026,796; which are hereby incorporated by reference.

EXAMPLES

These examples are provided to assist a person skilled in the art with understanding this invention. The particular reactants, conditions, and the like are intended to be merely illustrative of this invention and are not meant to be construed as unduly limiting the reasonable scope of this invention.

EXAMPLE I: Screening of Reaction Systems

Several reaction systems were tested for alkene addition activity. Solutions containing the reaction system components as listed below in Table I were tested in 250 mL sealed bottles. These bottles were sealed under anhydrous and oxygen-free conditions. Any solid components were placed in the bottle prior to sealing. All of the reaction system liquid components were introduced via syringe into the sealed bottle. The bottles were then agitated to thoroughly mix the contents. The bottles were then heated in an oil bath to a temperature of about 95° C. Dried, polymerization grade propylene was then introduced to the bottle by bubbling it through the reaction system. Periodically, gas samples were removed from the reaction system and analyzed by an HP 5890 gas chromatograph which was equipped with a flame ionization chamber and a capillary column. This gas chromatograph was programmed to start at 45° C. for 6 minutes with a 15° C. per minute increase to 145° C.

TABLE I

| Run | Reaction System Components | Mole Ratio[1] | Activity[2] |
|---|---|---|---|
| 11 | n-BuLi[3] | NA | No |
| 12A | TMEDA[4] + n-BuLi | 10:1 | Yes |
| 12B | TMEDA + n-BuLi | 1:1 | Yes |
| 12C | TMEDA + n-BuLi | 1:10 | Yes |
| 13 | TMEDA + s-BuLi[5] | 10:1 | Yes |
| 14A | DME[6] + n-BuLi | 10:1 | No |
| 14B | DME + n-BuLi | 1:1 | No |
| 14C | DME + n-BuLi | 1:10 | No |
| 15A | THF[7] + n-BuLi | 10:1 | No |
| 15B | THF + n-BuLi | 1:1 | No |
| 15C | THF + n-BuLi | 1:10 | No |

[1]This is the molar ratio of the first component (if any) to the BuLi component.
[2]Activity was determined by using a gas chromatograph. A "yes" means that 4-methyl-1-pentene was detected (4-methyl-1-pentene is the dimerization product of propylene). A "no" means that there was not any 4-methyl-1-pentene detected.
[3]n-butyl lithium.
[4]tetramethylethylenediamine.
[5]sec-butyl lithium.
[6]Bis(1,2-dimethoxy)ethane ($CH_3OCH_2CH_2OCH_3$).
[7]tetrahydrofuran.

As can be seen from the data in Table I, a reaction system that comprised both a hydrocarbon alkali metal compound and a nitrogen-containing compound showed some activity (see Runs 12A–13). Furthermore, those reaction systems which did not contain the proper components failed to show any activity (see Runs 11, and 14A–15C).

EXAMPLE II: Production of 4-methyl-1-pentene

A reaction system comprising tetramethylethylenediamine and n-butyl lithium was further tested for reaction rate and selectivity. These components were placed in a one liter, stainless steel, stirred tank reactor. Dried, polymerization grade propylene was also added to the reactor through a pressurized metered tank. The reactor was then heated to a temperature of about 95° C. The reactor pressure was in the range of about 600 to 650 psig. Periodically, gas samples were removed from the reaction system and analyzed by an HP 5890 gas chromatograph which was equipped with a flame ionization chamber and a capillary column. This gas chromatograph was programmed to start at 45° C. for 6 minutes with a 15° C. per minute increase to 180° C.

TABLE II

| Run | Mole Ratio[1] | Reaction Rate[2] | Selectivity[3] |
|---|---|---|---|
| 21 | 3:1 | 0.18 | 20 |
| 22 | 2:1 | 0.17 | 40 |
| 23 | 1.5:1 | 0.28 | 100 |
| 24 | 1:1 | 0.22 | 80 |
| 25 | 0.5:1 | 0.10 | 30 |

[1]This is the molar ratio of TMEDA to n-BuLi.
[2]This is defined as the number of moles of 4-methyl-1-pentene produced per the number of moles of lithium per hour. (moles of 4MP1/(moles Li × number of hours).
[3]This is defined as the ratio of the amount of 4MP1 (by weight) to the amount of 4MP2 (by weight).

As can be seen from the above data, a molar ratio of 1.5 TMEDA to 1 n-butyl lithium seems to be best when making 4-methyl-1-pentene (see Run 23). This is illustrated in Run 23 by the high reaction rate and the high selectivity. High selectivity is especially important because of the difficulty of separating 4-methyl-1-pentene and 4-methyl-2-pentene.

That which is claimed is:

1. A process to produce a propylene-alpha-olefin dimerization or codimerization product said process comprising contacting:
   a hydrocarbyl alkali metal compound; with
   a nitrogen-containing compound wherein said nitrogen-containing compound has one of the following formulas

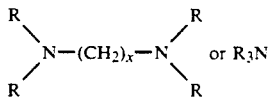

wherein each R group is independently selected from the group consisting of hydrogen and alkyls of 1 to 20 carbon atoms, inclusive and x is an integer between 1 and 10 inclusive;
   in the presence of propylene and another alpha-olefin;
   and recovering said propylene-alpha-olefin product.

2. A process according to claim 1 wherein said contacting is carried out in the presence of a catalytic support.

3. A process according to claim 2 wherein said catalytic support is selected from the group consisting of alkali metal carbonates, silicas, aluminas, alumina-silicas, alumina-phosphates, and mixtures thereof.

4. A process according to claim 2 wherein said catalytic support comprises potassium carbonate.

5. A process according to claim 1 wherein said hydrocarbyl alkali metal compound is selected from the group consisting of methyl lithium, ethyl lithium, propyl lithium, butyl lithium, butyl sodium, butyl potassium, butyl rubidium, butyl cesium, benzyl lithium, phenyl lithium, and mixtures thereof.

6. A process according to claim 1 wherein said hydrocarbyl alkali metal compound is butyl lithium.

7. A process according to claim 1 wherein said nitrogen-containing compound is selected from the group consisting of tetramethylethylenediamine, trimethylenediamine, triethylamine, and mixtures thereof.

8. A process according to claim 1 wherein said nitrogen-containing compound is tetramethylethylenediamine.

9. A process according to claim 1 wherein said alpha-olefin is selected from the group consisting of propylene, isobutylene, 1-butene, 3-methyl-1-butene, 1-pentene, 3-methyl-1-pentene, 4-methyl-1-pentene, 1-hexene, 3-ethyl-1-hexene, 1-octene, 1-decene, and mixtures thereof.

10. A process according to claim 1 wherein said contacting takes place at a temperature between −50° and 350° C. and a pressure between atmospheric and 10,000 psig.

11. A process according to claim 1 wherein the molar ratio of said nitrogen-containing compound to hydrocarbyl alkali metal is in the range of 3:1 to 0.5:1.

12. A process to produce a 4-methyl-1-pentene alkene addition product said process consisting essentially of:
   (a) contacting n-butyl lithium with tetramethylethylenediamine in the presence of propylene wherein the molar ratio of propylene to lithium is greater than 1:1; and thereafter
   (b) recovering an allyl/lithium/tetramethylethylenediamine complex; and thereafter
   (c) contacting said allyl/lithium/tetramethylethylenediamine complex with propylene; and
   (d) recovering said 4-methyl-1-pentene.

* * * * *